United States Patent [19]

Sheahon

[11] Patent Number: 5,087,262
[45] Date of Patent: Feb. 11, 1992

[54] AMNIOTIC MEMBRANE PERFORATOR

[76] Inventor: John A. Sheahon, U-2, Rte. 4, Lake Lotawana, Mo. 64063

[21] Appl. No.: 505,692

[22] Filed: Apr. 6, 1990

[51] Int. Cl.$^5$ ............................................. A61B 17/24
[52] U.S. Cl. .................................. 606/125; 606/119; 604/115
[58] Field of Search ................. 606/125, 119; 604/22, 604/46–48, 54, 55, 115, 272–274; 128/754

[56] References Cited

U.S. PATENT DOCUMENTS

| | | | |
|---|---|---|---|
| 2,660,169 | 11/1953 | Malm | 604/115 |
| 3,548,830 | 12/1970 | Goey et al. | 606/125 |

FOREIGN PATENT DOCUMENTS 2139901 11/1984 United Kingdom ................ 604/273

Primary Examiner—Stephen C. Pellegrino
Assistant Examiner—Steven J. Shumaker
Attorney, Agent, or Firm—Michael Yakimo, Jr.

[57] ABSTRACT

An amniotic membrane perforator includes an elongated shaft having a pair of spaced apart lobes at the distal end thereof relative to the user. A pair of tines are positioned between the lobes. Upon insertion of the perforator into the vaginal canal the lobes depress the amniotic sac so as to present a portion of the sac tissue to the tines for subsequent puncture.

2 Claims, 1 Drawing Sheet

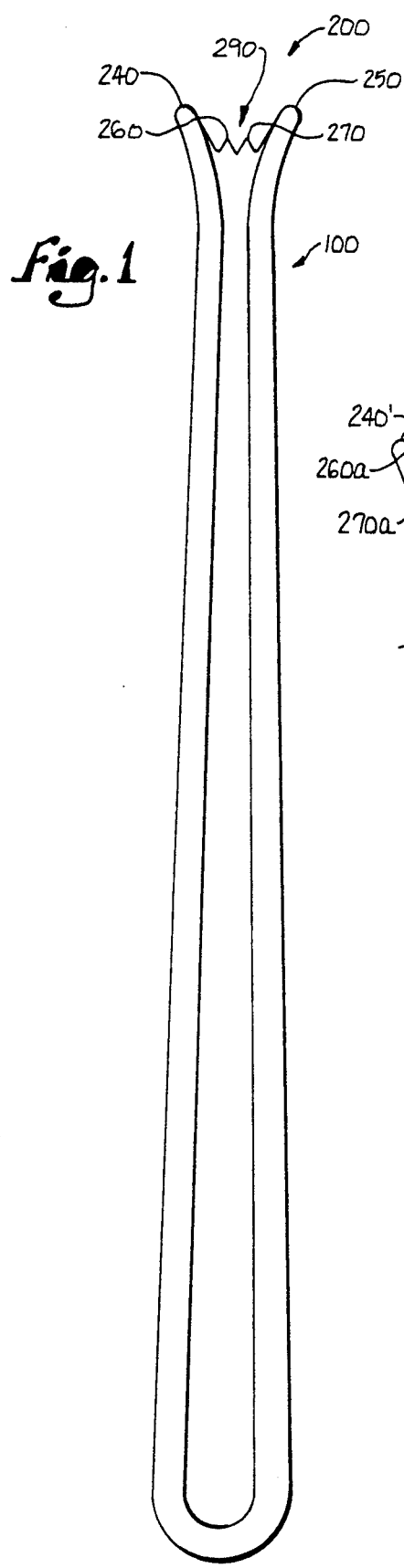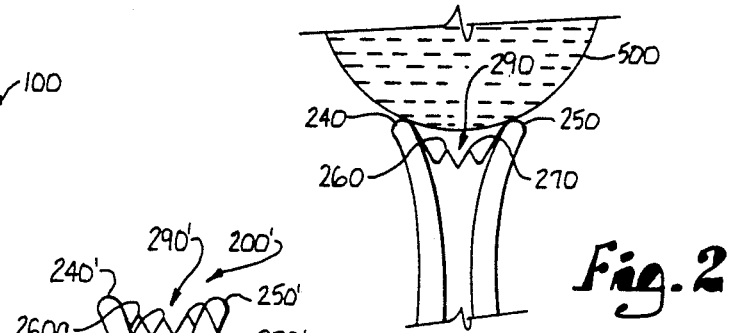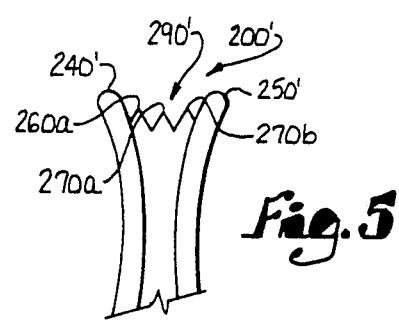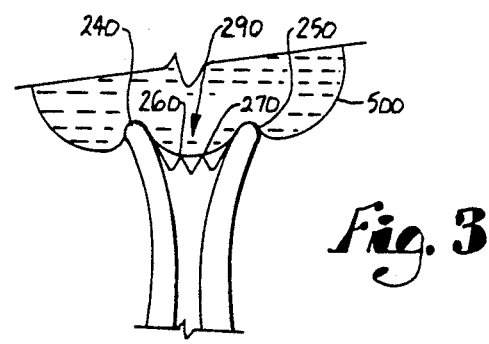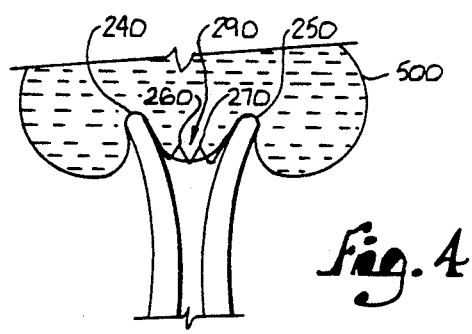

5,087,262

AMNIOTIC MEMBRANE PERFORATOR

BACKGROUND OF THE INVENTION

This invention relates to a medical device and more particularly to an amniotic membrane perforator for rupturing the amniotic sac.

During the labor stage of child birth, it may be necessary to rupture the "bag of water" or amniotic sac so as to enhance the birthing process. Such a rupture allows the amniotic fluid to escape from the sac so as to enhance uterine contractions. Previous "hook"-types of instruments have been used by the physician so as to assist in such rupturing. One type of amniotic membrane perforator has a hook at the end thereof. The physician tries to hook a part of the amniotic sac so as upon pulling it will rupture the same.

Problems have arisen in use of such a hook as a smooth surface of the sac is difficult to obtain purchase thereon and therefore a subsequent puncture. Moreover, the hook may pierce the sac and engage a part of the fetus. Also, upon withdrawal of the hook from the patient it may grasp the cervix or the surrounding tissue thereof.

In response thereto, I have invented a novel amniotic sac perforator which alleviates these problems. Such a perforator includes a pair of laterally-spaced prongs with a puncture device therebetween. The prongs depress the sac so as to present a portion of the amniotic sac tissue therebetween. Upon further depression of the sac by the prongs the puncture portions will pierce the amniotic sac. The use of the prongs surrounding the puncture elements precludes the undesirable snagging of the sac, fetus, cervix and surrounding tissue thereof.

Accordingly, it is a general object of this invention to provide a tissue/amniotic membrane perforator.

Another object of this invention is to provide an amniotic membrane perforator which precludes undesirable snagging of the amniotic sac.

A more particular object of this invention is to provide an amniotic perforator which punctures the sac rather than rips the sac tissue.

Still another particular object of this invention is to provide an amniotic perforator which precludes undesirable snagging of the fetus, cervix and surrounding tissue.

Other objects and advantages of this invention will become apparent from the following description taken in connection with the accompanying drawings, wherein is set forth by way of illustration and example, an embodiment of this invention.

BRIEF DESCRIPTION OF THE DRAWINGS

FIG. 1 illustrates the amniotic membrane perforator on an enlarged scale;

FIG. 2 is a fragmentary view of the amniotic membrane perforator illustrated in FIG. 1 with the amniotic sac being shown diagrammatically thereof and showing the initial relationship between the perforator and the sac;

FIG. 3 is a view similar to that of FIG. 2 and showing a depression of the amniotic sac by the prong members thereof;

FIG. 4 is a view similar to that of FIGS. 2 and 3 and showing a further depression of the amniotic sac being punctured; and FIG. 5 is a fragmentary view showing an alternative puncture assembly.

DESCRIPTION OF THE PREFERRED EMBODIMENT

Turning more particularly to the drawings, FIG. 1 illustrates my novel amniotic membrane perforator 10 on an enlarged scale so as to assist in illustration and description.

As shown, the device includes an elongated shaft 100 having a sac perforating assembly 200 at the end thereof. The perforating assembly 200 comprises a pair of laterally spaced apart lobes 240, 250 or prongs with a pair of puncture tines 260, 270 positioned therebetween. The lobes 240, 250 extend beyond the tines 260, 270 and present a capture area 290 for extension of a portion of the sac therein. The lobes are preferably rounded at the free ends thereof so as to preclude an undesirable interaction, such as snagging, puncture and the like with the amniotic sac, fetus, and surrounding tissue.

FIG. 2 illustrates a portion of the assembly 200 with the amniotic sac 500 being diagrammatically shown for purposes of illustration. To puncture the amniotic sac the physician inserts the perforator 100 in the birth-/vaginal canal until the lobes 240, 250 touch the amniotic sac 500 as tactilely sensed by the physician and as shown in FIG. 2. Once contact is made the perforator portion 200 is further inserted so as to further depress the laterally spaced apart lobes 240, 250 into the amniotic sac as shown in FIG. 3. As such, a portion of the tissue 510 of the amniotic sac is positioned in the capture area 290 between the lobes 240, 250. The lobe extension past the tines places the tissue in a desired position adjacent the tines 260, 270 prior to puncture.

Accordingly, upon further penetration of the device 100, the lobes 240, 250 further depress a portion of the sac tissue into the capture area 290 such that the tines functionally engage the tissue of the amniotic sac 500 and pierce the tissue thereof (FIG. 4). Once so pierced the amniotic fluid escapes to enhance the uterine contractions.

The use of the lobes 240, 250 capture area 290 and tines 260, 270 combination presents a safe, effective apparatus for rupturing the amniotic sac. Moreover, this use delimits the possibility of undesirable interaction of the perforating assembly 200 with the sac 500, fetus, cervix and surrounding vaginal tissue.

An alternative perforating assembly 200' is shown in FIG. 5 in which three tines 260a, 270a, 270b are used in a manner as above described with similar advantages and results.

It is to be understood that while certain forms of this invention have been illustrated and described, they are not limited thereto, except in so far as such limitations are included in the following claims and allowable functional equivalents thereof.

Having thus described the invention, what is claimed as new and desired to be secured by Letters Patent is:

1. A perforator for penetrating amniotic sac tissue of a patient comprising:
   an elongated shaft having proximal and distal ends, said shaft having a configuration for insertion into a vaginal canal of the patient with a length to allow said distal end to be positioned adjacent the amniotic sac while said proximal end is positioned exterior of the vaginal canal; perforating means at said distal end of said shaft comprising:

a pair of spaced-apart lobes extending from said distal end of said shaft and diverging from a central longitudinal axis of said shaft, said lobes extending toward the amniotic sac upon said positioning of said shaft in the canal by a user, said lobes having a configuration hindering a puncture of the amniotic sac tissue;

said diverging lobes defining an area therebetween for the reception of a downwardly bulging portion of the adjacent amniotic sac between said lobes upon an urging of said lobes against the sac by a first manipulation of said proximal end of said shaft by the user;

puncture means extending from said distal end of said shaft and fixed between said lobes, said lobes of said shaft extending beyond said puncture means to allow for said bulging of the sac between said lobes upon said first user manipulation of said distal end prior to a subsequent piercing of the bulging portion of the sac between said lobes by said puncture means upon a second manipulation of said proximal shaft end by the user.

2. The apparatus as claimed in claim 1 wherein said puncture means comprises at least one tine positioned between said lobes, said tine piercing said tissue.

* * * * *

UNITED STATES PATENT AND TRADEMARK OFFICE
CERTIFICATE OF CORRECTION

PATENT NO. : 5,087,262
DATED : February 11, 1992
INVENTOR(S) : John A. Sheahon

It is certified that error appears in the above—identified patent and that said Letters Patent is hereby corrected as shown below:

Column 2, line 66, after "canal;" begin a new paragraph.

Column 4, line 13, delete "said tissue" and substitute --sac tissue-- therefor.

Signed and Sealed this

Twentieth Day of April, 1993

Attest:

MICHAEL K. KIRK

*Attesting Officer*  Acting Commissioner of Patents and Trademarks